US00PP31100P2

(12) United States Plant Patent
Delabroye

(10) Patent No.: US PP31,100 P2
(45) Date of Patent: Nov. 19, 2019

(54) ***HEUCHERA* PLANT NAMED 'HIGH HOPES'**

(50) Latin Name: ***Heuchera* hybrid**
Varietal Denomination: High Hopes

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 0 days.

(21) Appl. No.: 16/350,617

(22) Filed: Dec. 11, 2018

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Heuchera* named 'High Hopes' that is characterized by its leaves that are very large in size, its leaves that are green-yellow in color with brown orange veins, its flowers that are creamy white in color, its healthy and vigorous growth habit and its high tolerance to heat.

2 Drawing Sheets

Botanical classification: *Heuchera* hybrid.
Cultivar designation: 'High Hopes'.

CROSS REFERENCE TO A RELATED APPLICATION

This application is related to a U.S. Plant Patent a for plant derived from the same breeding program that is entitled *Heuchera* Plant Named 'Vulcano' (U.S. Plant Pat. No. 20,429).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Heuchera* of hybrid origin, botanically known as a *Heuchera* and is hereinafter referred to by its cultivar name 'High Hopes'.

The new cultivar was discovered as a chance seedling in a trial field by the Inventor in Hantay, France in May of 2016. The trial field contained hundreds of proprietary *Heuchera* seedlings from the Inventor's breeding program and other cultivars. The parentage of 'High Hopes' is therefore unknown.

Asexual propagation of the new cultivar was first accomplished under the direction of the Inventor by tissue culture initiated from meristem tissue in summer of 2016 in Rijswijk, The Netherlands. Asexual propagation of the new cultivar by tissue culture has determine that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'High Hopes' as a new and unique cultivar of *Heuchera*.

1. 'High Hopes' exhibits leaves that are very large in size.
2. 'High Hopes' exhibits leaves that are green-yellow in color with brown orange veins.
3. 'High Hopes' exhibits flowers that are creamy white in color.
4. 'High Hopes' exhibits healthy and vigorous growth habit.
5. 'High Hopes' exhibits a high tolerance to heat.

'High Hopes' can be most closely compared to the *Heuchera* cultivars 'Tiramisu' and 'Bronze Beauty' (not patented). 'Tiramisu' is similar to 'High Hopes' in foliage coloration. 'Tiramisu' differs from 'High Hopes' in having a less robust plant habit, leaves that are much smaller in size and a less vigorous growth habit. 'Bronze Beauty' is similar to 'High Hopes' in overall plant shape and foliage shape and size. 'Bronze Beauty' differs from 'High Hopes' in having foliage colors that are bronze and light brown in color.

BRIEF DESCRIPTION OF THE DRAWINGS

The accompanying colored photograph illustrates the overall appearance and distinct characteristics of the new *Heuchera*. The photograph was taken of a plant 18 months in age as grown in a greenhouse in a 30-cm container in Hantay, France.

The photograph in FIG. 1 provides a side view of the plant of 'High Hopes' in bloom.

Figure 1:
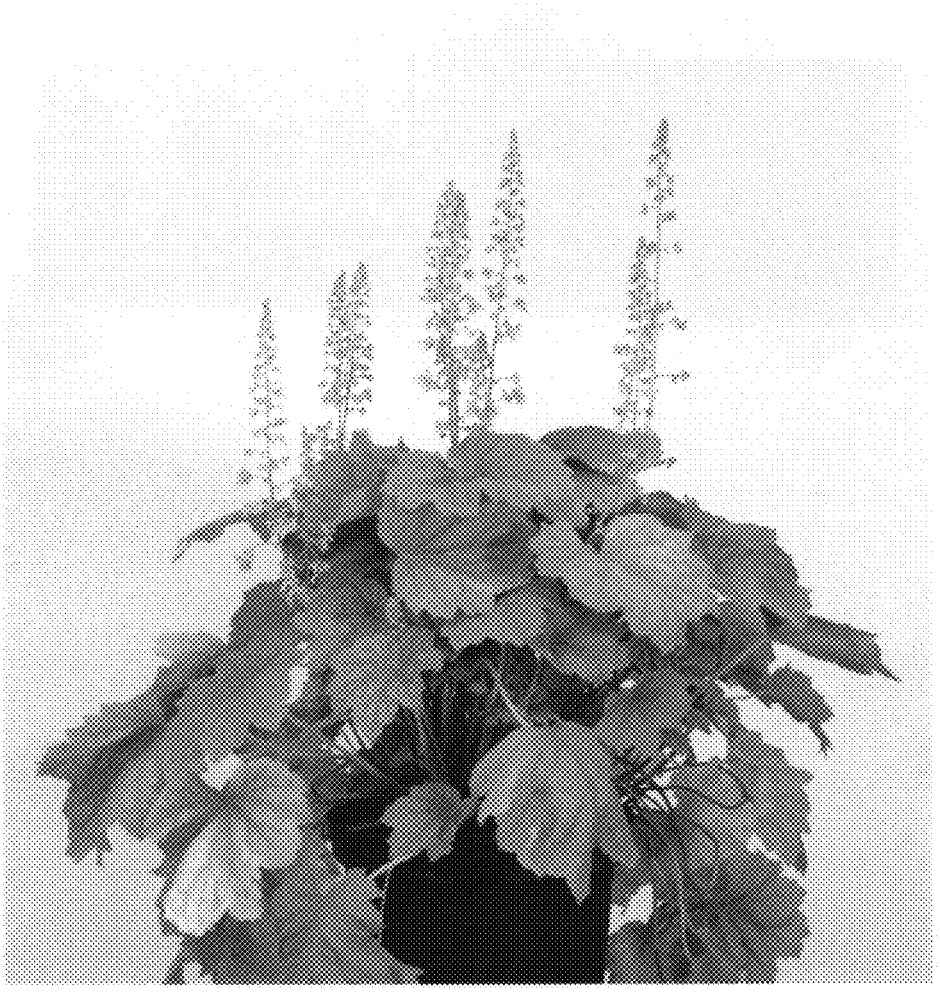
Figure 2:
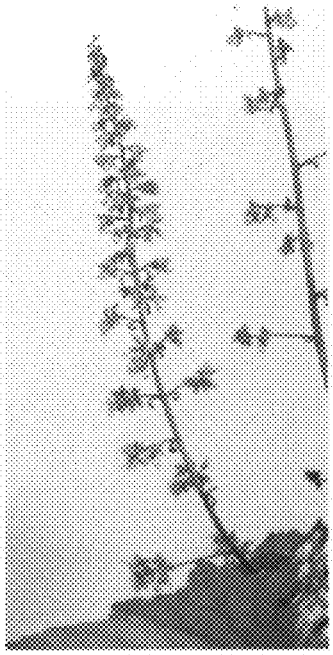

The photograph in FIG. 2 provides a close up of the inflorescence of 'High Hopes'.

Figure 3:
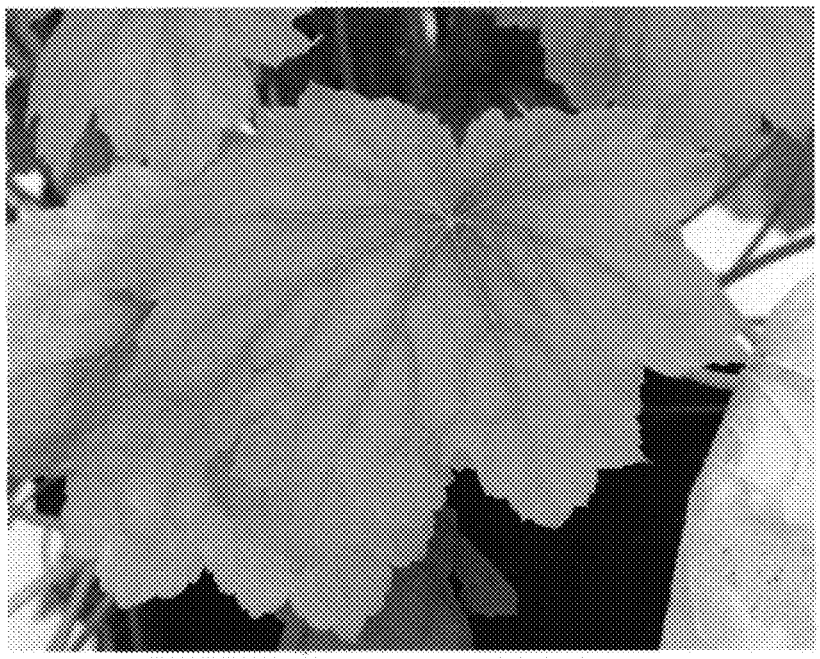

The photograph in FIG. 3 provides a close up of the foliage of 'High Hopes'.

The colors in the photograph are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 30-cm containers in Hantay, France. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—An average of 6 weeks in May and June in Hantay, France.

*Plant type*.—Herbaceous perennial.

*Plant habit*.—Flattened globular with inflorescences held above the foliage.

*Height and spread*.—An average of 70 cm in height and 80 cm in width in the landscape.

*Hardiness*.—At least in U.S.D.A. Zones 3 to 9.

*Environmental stress*.—Tolerant to high heat.

*Diseases and pests*.—No susceptibility or resistance to pests or diseases has been observed.

*Root description*.—Fibrous roots on woody rootstalks, 158D in color.

*Propagation*.—Tissue culture.

*Root development*.—An average of 13 weeks to fully develop from a tissue culture plug in a 7-cm or larger container.

*Growth rate*.—Moderate to high.

Stem description (peduncle, flowering stem):

*Shape*.—Round.

*Stem color*.—N144D.

*Stem size*.—An average of 4 mm in diameter and 61.3 cm in length.

*Stem strength*.—Moderately strong.

*Stem aspect*.—Primary flowering stems grow at an angle of 80° (0°=horizontal), secondary flowering stems grow at an angle of 75° (0°=horizontal).

*Stem surface*.—Slightly glossy, densely covered with short soft glandular hairs; an average of 0.3 mm in length and N144D in color.

*Stem number*.—Average of 11 flowering stems.

*Branching habit*.—Flowering stems emerge from basal rosette.

Foliage description:

*Leaf shape*.—Near globular to reniform.

*Leaf division*.—Simple.

*Leaf base*.—Hastate, lobes free to touching.

*Leaf apex*.—Obtuse to broad acute with a very small abruptly acute outer tip.

*Leaf venation*.—Laciniate, upper surface N144A, lower surface 145B.

*Leaf margins*.—Dentate-crenate with abruptly acute tips on each tooth, slightly undulate.

*Leaf attachment*.—Petiolate.

*Leaf arrangement*.—Alternate in basal rosettes.

*Leaf lobes*.—Lobed, an average of 7 lobes, shallow in depth, divergent.

*Leaf surface*.—Both surfaces matte, non-rugose and pubescent, moderately to densely covered with very short strigose hairs an average of 0.5 mm in length and 157D in color.

*Leaf color*.—Young upper and lower surface is 166C, fading to N144C towards the margins, veined 145C, mature upper surface N144A, fading to N144D towards the margins and top, area around veins occasionally tinged with 165A, mature lower surface 145B, area around veins occasionally tinged 166D.

*Leaf size*.—An average of 17.2 cm in length and 18.3 cm in width.

*Leaf quantity*.—An average of 14 per basal rosette.

*Petioles*.—An average of 29.2 cm in length and 4.5 mm in diameter, upper and lower surface color is 145A, both surfaces are matte, moderate in strength, densely covered with soft hairs an average of 1 mm in length and NN155D in color.

*Stipules*.—Leafy stipule at the base of each leaf, in basal leaves average length 1.6 cm, average width 0.3 cm, tip acute, 185C and 187A in color.

Flower description:

*Inflorescence type*.—Numerous small bell-shaped flowers arranged on panicles on peduncles emerging from a basal rosette.

*Inflorescence size*.—An average of 27.6 cm in height and 8.8 cm in diameter.

*Inflorescence number*.—An average of 10.

*Flower fragrance*.—None.

*Flower quantity*.—Average of 350 flowers per flowering stem.

*Flower lastingness*.—Average of one week.

*Flower buds*.—Ovate in shape, an average of 3 mm in length and 1.5 mm in diameter, color; 155C, tinged 145A at the top, lower half 150B, surface is matte and densely covered with very short glandular hairs; an average of 0.3 mm in length and too small to measure color.

*Flower aspect*.—Upright, outwardly and nodding.

*Flower type*.—Single, campanulate.

*Flower size*.—Average of 4 mm in height and diameter, 6.5 mm in length.

*Petals*.—Average of 5, rotate arrangement and implanted in the hypanthium at base, narrow oblanceolate in shape and curled, margin is entire, apex is narrow acute, base is narrow attenuate, upper and lower surface is glabrous, smooth and matte, color of upper and lower surface when opening and when fully open; NN155D, an average of 3 mm in length and 0.75 mm in width.

*Calyx*.—Campanulate, sepals fused to hypanthium, 4 mm in length and 3.5 mm in diameter.

*Sepals*.—An average of 5, lower 62.5% fused into campanulate hypanthium, oblong in shape, an average of 4 mm in length and 1.75 mm in width, margin is entire and fused into hypanthium, apex is obtuse, fused base, color; when opening upper and lower surface 155C, tinged 145A, lower half 150B, fully open upper and lower surface between 150D and 155C, tinged 145A to 145B, lower half N144D, both surfaces are matte, lower surface is densely covered with very short glandular hairs an average of 0.3 mm in length and to small to measure color.

*Pedicels*.—An average of 3.5 mm in length and 0.5 mm in diameter, N144D in color, primary flower aspect straight on top of secondary pedicel, secondary and tertiary flower aspect is 45°, moderate in strength, surface matte and densely covered with very short soft glandular hairs; average of 0.2 mm in length and to small to measure color.

Reproductive organs:

*Gynoecium*.—Pistils; 2, 4 mm in length, stigma; club-shaped, NN155D in color, 0.2 mm in diameter, style; an average of 3.75 mm in length and NN155D in color, ovary; 150B in color.

*Androecium*.—Stamens; 5, anthers; broad oblong in shape, about 0.5 mm in length and width, N170C in color, filament; 2.5 mm in length and NN155D in color, pollen; low to moderate in quantity and 175B in color.

*Seed/fruit*.—No fruit or seeds were observed to date.

It is claimed:

1. A new and distinct cultivar of *Heuchera* plant named 'High Hopes' as herein illustrated and described.

* * * * *